(12) United States Patent
Olstad et al.

(10) Patent No.: US 6,350,238 B1
(45) Date of Patent: Feb. 26, 2002

(54) REAL-TIME DISPLAY OF ULTRASOUND IN SLOW MOTION

(75) Inventors: Bjorn Olstad, Stathelle; Hans Torp, Trondheim, both of (NO)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/432,060

(22) Filed: Nov. 2, 1999

(51) Int. Cl.[7] .................................................. A61B 8/00
(52) U.S. Cl. ........................ 600/437; 600/443; 600/453
(58) Field of Search ................................. 600/443, 447, 600/454, 450, 451, 458, 437; 358/111; 364/414; 128/916

(56) References Cited

U.S. PATENT DOCUMENTS

| | | | |
|---|---|---|---|
| 4,572,202 A | * 2/1986 | Thomenius | 600/437 |
| 5,099,847 A | * 3/1992 | Powers et al. | 600/443 |
| 5,666,955 A | * 9/1997 | Kondo et al. | 600/440 |
| 5,961,462 A | * 10/1999 | Loupas et al. | 600/453 |
| 6,086,537 A | * 7/2000 | Urbano et al. | 600/443 |

\* cited by examiner

*Primary Examiner*—Marvin M. Lateef
*Assistant Examiner*—Ali M. Imam
(74) *Attorney, Agent, or Firm*—McAndrews Held & Malloy, Ltd.; Peter J. Vogel; Michael A. Dellapenna

(57) ABSTRACT

A system and method for acquiring ultrasound information at an acquisition rate and displaying at least a portion of the acquired ultrasound information at a display rate that is slower than the acquisition rate is disclosed. Ultrasound information may be continuously acquired and stored at a frame-rate that is greater than the perception rate of the human eye. At least a portion of the acquired ultrasound information is displayed at a frame-rate that allows human perception. Acquisition and display are synchronized from time-to-time upon satisfaction of a synchronization condition. The synchronization condition may be related to a predetermined time interval or a triggering event generated by or through triggering generated by, for example, a physiological event detected in, for example, an ECG trace. Acquired ultrasound information is, thus, displayed in a real-time slow motion manner that maintains real-time synchrony and yet provides a display rate that is lower than the acquisition rate and preferably lower than the maximum perception rate of the human eye.

38 Claims, 11 Drawing Sheets

REAL-TIME DISPLAY OF ULTRASOUND IN SLOW MOTION

CROSS REFERENCE TO RELATED APPLICATIONS

None.

STATEMENT REGARDING FEDERALLY SPONSORED RESEARCH & DEVELOPMENT

None.

BACKGROUND OF THE INVENTION

The present invention relates to ultrasound systems which image anatomical structures and the movement thereof. More particularly, the present invention relates to a method and apparatus for displaying in real-time a slow motion ultrasound image.

Recent advances in ultrasound technology have made it possible to acquire ultrasound images with frame-rates that exceed the limitations given by the human eye and current video standards such as PAL and NTSC. The human eye recognizes about 30–50 frames per second, but 100–300 images can be acquired each second with current high performance ultrasound systems.

The increase in frame-rate offers significant new clinical information because physiological events in, for example, cardiology can be extremely rapid and cannot be resolved with frame-rates less than 30 frames per second. An example of a physiological event that requires a high frame-rate to resolve is cardiac valve motion. At 30 frames per second, only a few image frames are available to study the opening of a valve. At 300 frames per second, one can study details in the motion pattern of the valve during the opening. Similarly, myocardial motion and contraction cannot be satisfactorily resolved at 30 frames per second. Tissue velocity imaging and strain rate imaging are difficult to grasp in real-time due to the rapid changes in color display. New techniques recently developed for blood motion imaging are capable of producing a 2D motion pattern of blood flow at for example 200 frames per second, well above the maximum perception rate of the human eye. These new techniques will therefore benefit from slow motion.

It is a limitation of current ultrasound systems that the additional information provided by high frame-rates cannot be satisfactorily visualized by the human eye or recorded on video during live scanning. A current procedure for visualizing high frame-rate ultrasound includes the steps of: acquiring and digitally storing ultrasound information, stopping the acquisition and replaying a stored period of ultrasound information in slow motion. The length of the stored period may coincide with a physical event, such as a heartbeat. A video recorder may be used to record the slow motion playback.

A further problem confronting the field is the live display of ultrasound diagnostic modalities that are too computationally intensive to allow the display to keep up with the acquisition rate. With current technologies, such a situation must be handled by either lowering the acquisition frame-rate, skipping frames in the display, or limiting viewing to a replay of data that is processed off-line in less than real-time.

A still further problem confronting the field is the need to acquire additional ultrasound information without changing the display during live scanning. For example, during stress echo analysis, it is desirable to have a continuous live display of high quality 2D images during scanning, but at the same time acquire additional information like tissue velocity imaging and strain rate imaging. It is also desirable to afford continuous live display while retrieving and accessing tissue velocity imaging and strain rate imaging to quantify wall motion and wall thickening.

U.S. Pat. No. 4,572,202 to Thomenious et al. describes a way to alternate between periodically acquiring ultrasound information at a rate which is greater than the perception rate of the human eye, recording the acquired information over a short period of time and displaying, in an off-line mode (as opposed to a live display), the recorded information at a lower rate than the acquisition rate. The period over which ultrasound information is acquired and recorded is triggered, for example, based on the trace produced on an electrocardiogram so that part of the cardiac cycle can be studied. The playback rate during display may be manually or automatically adjusted. While providing clinically useful information, the system described in the Thomenious patent has a number of limitations, such as difficulty in displaying complete heart cycles. Also, in the system of the Thomenious patent, ultrasound information is only recorded periodically during short time intervals, relatively long time lags exist between acquisition and display, variations in heart rate from beat to beat may cause "flicker" in the display, and ultrasound information is not acquired, recorded or displayed during the time between recording periods.

A need remains for an improved ultrasound system to overcome the above-identified difficulties and limitations.

BRIEF SUMMARY OF THE INVENTION

A system and method are provided for acquiring ultrasound information at an acquisition rate and displaying at least a portion of the acquired ultrasound information at a display rate that is slower than the acquisition rate. Ultrasound information may be continuously acquired and stored at a frame-rate that is greater than the perception rate of the human eye. At least a portion of the acquired ultrasound information is displayed at a frame-rate that allows human perception. Acquisition and display are synchronized from time-to-time upon satisfaction of a synchronization condition. The synchronization condition may be related to a predetermined time interval or a triggering event generated by or through triggering generated by, for example, a physiological event detected in, for example, an ECG trace. Acquired ultrasound information is, thus, displayed in a real-time slow motion manner that maintains real-time synchrony and yet provides a display rate that is lower than the acquisition rate and preferably lower than the maximum perception rate of the human eye.

The real-time slow motion display of ultrasound information may be displayed alone or simultaneously with a display of the ultrasound information having a display rate equal to the acquisition rate. A real-time slow motion display may also be combined with a triggered M-mode display that allows a user to manually select triggering events or time intervals.

According to another aspect of a preferred embodiment of the present invention, the acquisition of ultrasound information may be performed according to a first acquisition mode during a first acquisition period and a second different mode during a second acquisition period. The ultrasound information acquired during the first acquisition period may be displayed at a display rate that is slower than the acquisition rate such that a portion of the ultrasound information acquired during the first acquisition period is displayed during the first acquisition period and a portion of the ultrasound information acquired during the first acquisition period is displayed during a second acquisition period. The ultrasound information acquired during the first acquisition period may be displayed separately or stored for off-line display.

According to another aspect of a preferred embodiment of the present invention, ultrasound information is acquired at an acquisition rate and processed at a processing rate that is lower than the acquisition rate and displayed at a display rate than is the same as or lower than the processing rate while acquisition of ultrasound information is ongoing. Acquisition and processing are synchronized from time-to-time in the manner described above.

Other objects, features, and advantages of the present invention will be apparent from the accompanying drawings and from the detailed description that follows below.

DETAILED DESCRIPTION OF THE INVENTION

A method and apparatus are described for continuously acquiring ultrasound information with a high frame-rate and displaying all or a portion of the acquired ultrasound information at a display rate that is lower than the acquisition rate while maintaining real-time synchrony. In the following description, numerous specific details are set forth in order to provide a thorough understanding of the preferred embodiments of the present invention. It will be apparent, however, to one of ordinary skill in the art that the present invention may be practiced without these specific details.

The present invention may be applied to any 2D ultrasound diagnostic imaging modality. The terms frame/image are used to denote any time instance of the ultrasound information such as a tissue frame, a color flow frame, a tissue velocity frame, etc. The frame/image can also include display of information computed from the ultrasonic data in real-time such as an image segmentation or Doppler derived quantity.

Figure 1:
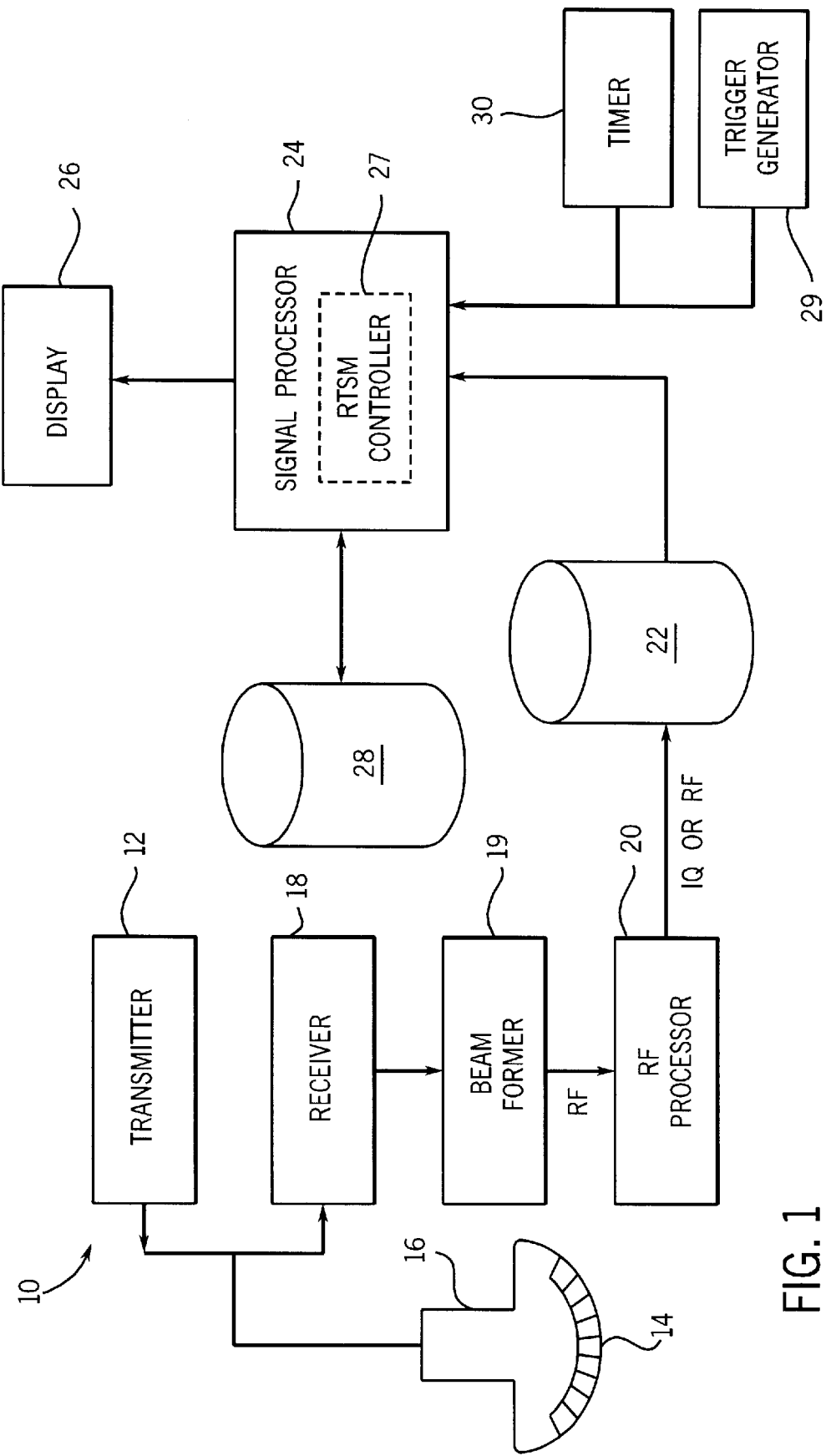
FIG. 1 illustrates a block diagram of an ultrasound imaging system according to a preferred embodiment of the present invention.

A block diagram for an ultrasound system (generally indicated at 10) according to a preferred embodiment of the present invention is shown in FIG. 1. The ultrasound system 10 may acquire ultrasound information according to any known scheme. The ultrasound system 10 includes a transmitter 12 which drives transducers 14 within a probe 16 to emit pulsed ultrasonic signals into a body. The ultrasonic signals are backscattered from structures in the body, like blood cells or muscular tissue, to produce echoes which return to the transducers 14. The echoes are detected by a receiver 18. The received echoes are passed through a beamformer 19, which performs beam forming and outputs an RF signal. The RF signal then passes through an RF processor 20. The RF signal data may then be routed directly to a buffer 22 for temporary storage. Alternatively, the RF processor 20 may include a complex demodulator (not shown) that demodulates the RF signal to form I, Q data pairs representative of the echo signals prior to temporary storage in buffer 22.

Ultrasound system 10 also includes a signal processor 24 to process the acquired ultrasound information (i.e., RF signal data or I, Q data pairs) and prepare frames of ultrasound information for display on display 26. The signal processor 24 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in buffer 22 during a scanning session and processed in less than real-time in a live or off-line operation as will be described in greater detail herein.

The ultrasound system 10 continuously acquires ultrasound information at a frame-rate that exceeds 30–50 frames per second—the maximum perception rate of the human eye. The acquired ultrasound information is displayed on display 26 at a slower frame-rate. The signal processor 24 includes a real-time slow motion controller (RTSM controller) 27 that controls which frames of acquired ultrasound information are to be displayed and the frame-rate of the display or display rate. A memory 28 is included for storing processed frames of acquired ultrasound information that are not scheduled to be displayed immediately. The RTSM controller 27 controls which frames are retrieved for display. Preferably the memory 28 is of sufficient capacity to store several seconds worth of frames of ultrasound information. The frames of ultrasound information are stored in a manner to facilitate retrieval thereof according to its order or time of acquisition. Memory 28 may comprise any known data storage medium. When the acquired ultrasound information is to be processed in less than real-time, the RTSM controller 27 may also control what ultrasound information is retrieved from buffer 22 for processing.

In order to allow the real-time slow motion display to catch up with the live acquisition that is ongoing and running with a higher frame-rate than the display, the RTSM processor 27 periodically synchronizes the display with the ongoing acquisition. Without synchronization, the display 26, which is presenting ultrasound information at a display rate with a slower frame-rate than the acquisition rate, would lag longer and longer behind the acquisition and the to have live feedback during slow motion display would be lost. Synchronization between acquisition and display may be accomplished in a triggered or non-triggered manner. Accordingly, ultrasound system 10 may include a trigger generator 29 and/or a timer 30 which sends a synchronization signal to RTSM controller 27. The operation of the trigger generator 29 and timer 30 are described below.

Figure 2:
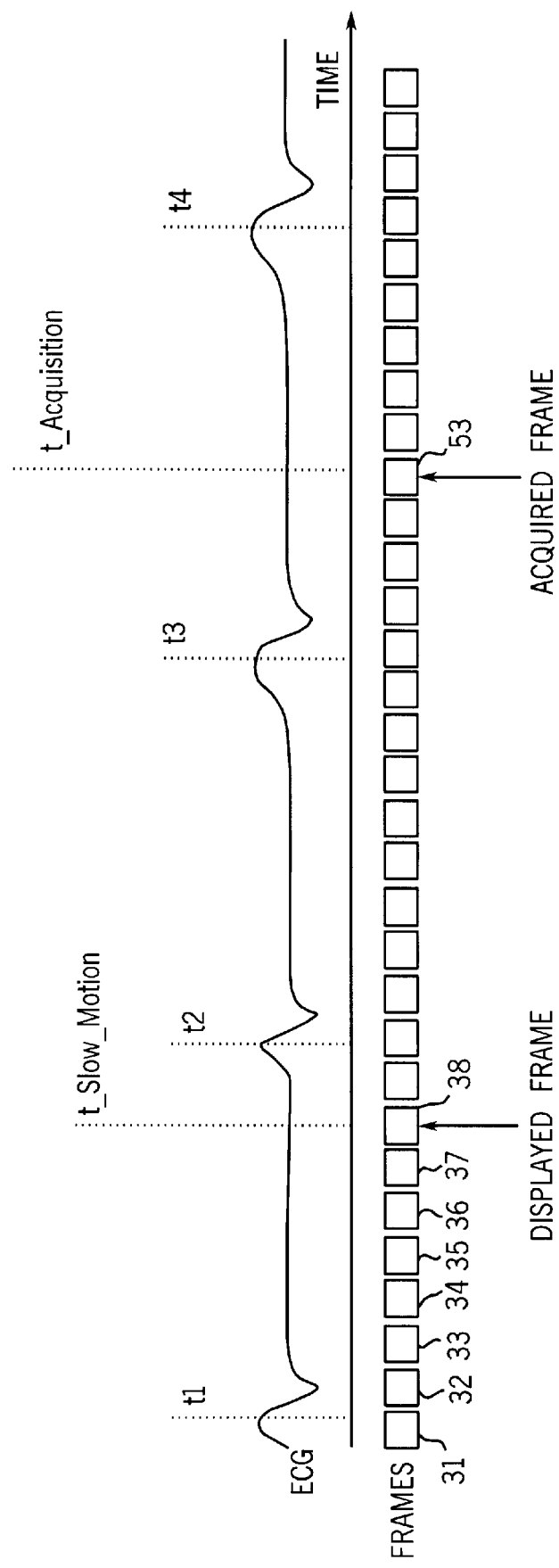
FIG. 2 illustrates a timing diagram of a procedure for synchronizing a real-time slow motion display of ultrasound data with ongoing acquisition of ultrasound information according to a preferred embodiment of the present invention.

FIG. 2 illustrates a triggered implementation of real-time slow motion. Triggering events is generated by the trigger generator 29 (shown in FIG. 1) at the time instances: t1, t2, t3, t4 and so on. By way of example only, a triggering event may be generated by QRS detection in an ECG trace as it is indicated in FIG. 2. Other triggering sources can also be used such as phono traces, external traces measuring physiological parameters such as pressure or parameters derived from the ultrasound information. A user may specify a slow motion factor which may be defined as a ratio between the acquisition frame-rate and the display frame-rate. The slow motion factor may have any value greater than one. Alternatively, the slow motion factor may be computed automatically in order to obtain a desired display frame-rate such as the frame-rate of a particular video standard. FIG. 1 illustrates an example where the slow motion factor equals 3.

As illustrated in FIG. 2, acquisition and display are synchronized at the first generated trigger event, t1. The image frame acquired at t1 (image frame 31) is displayed immediately. Subsequent frames 32, 33, 34, 35, 36, 37 and 38, etc. are not displayed immediately as they are acquired but are instead displayed with a slow motion factor of 3. Thus, as shown in FIG. 1, at acquisition time t_Acquisition, the corresponding acquired frame 53 is stored in a memory 28, but not immediately displayed. Instead, a corresponding time, t_Slow_Motion, is computed as:

$$t\_Slow\_Motion = t1 + ((t\_Acquisition - t\_Acquisition\_Start)/(Slow\ motion\ factor))$$

where t_Acquisition_Start denotes the acquisition time (t_Acquisition) when the current slow motion segment was started. The image frame 38 corresponding to t_Slow_Motion is thus displayed at time t_Acquisition. This is repeated as long as t_Slow_Motion is less than t2. With a slow motion factor of 3 this will cause the heartbeat between t1 and t2 to be displayed in a 3 times longer time period which will allow for better visual appreciation of, for example, rapid movements or tissue velocities in the image sequence.

Synchronization, which allows the display catch up with the acquisition, can be implemented in a number of alternative ways. One technique is to detect when t_Slow_Motion is greater than or equal to t2 (t_Slow_Motion≧t2) and then at that point resetting t1 to the last detected trigger event, resetting t_Acquisition_Start to the current acquisition time (t_Acquisition) and recomputing t_Slow_Motion using the updated values. These steps are then repeated each time t_Slow_Motion is between t2 and t3 (or greater or equal to t2). This synchronization technique will make sure that the slow motion display runs in a smooth cyclic manner and that the display never will lag behind the acquisition by more than approximately the duration of a cardiac cycle multiplied by the slow motion factor.

Figure 3:
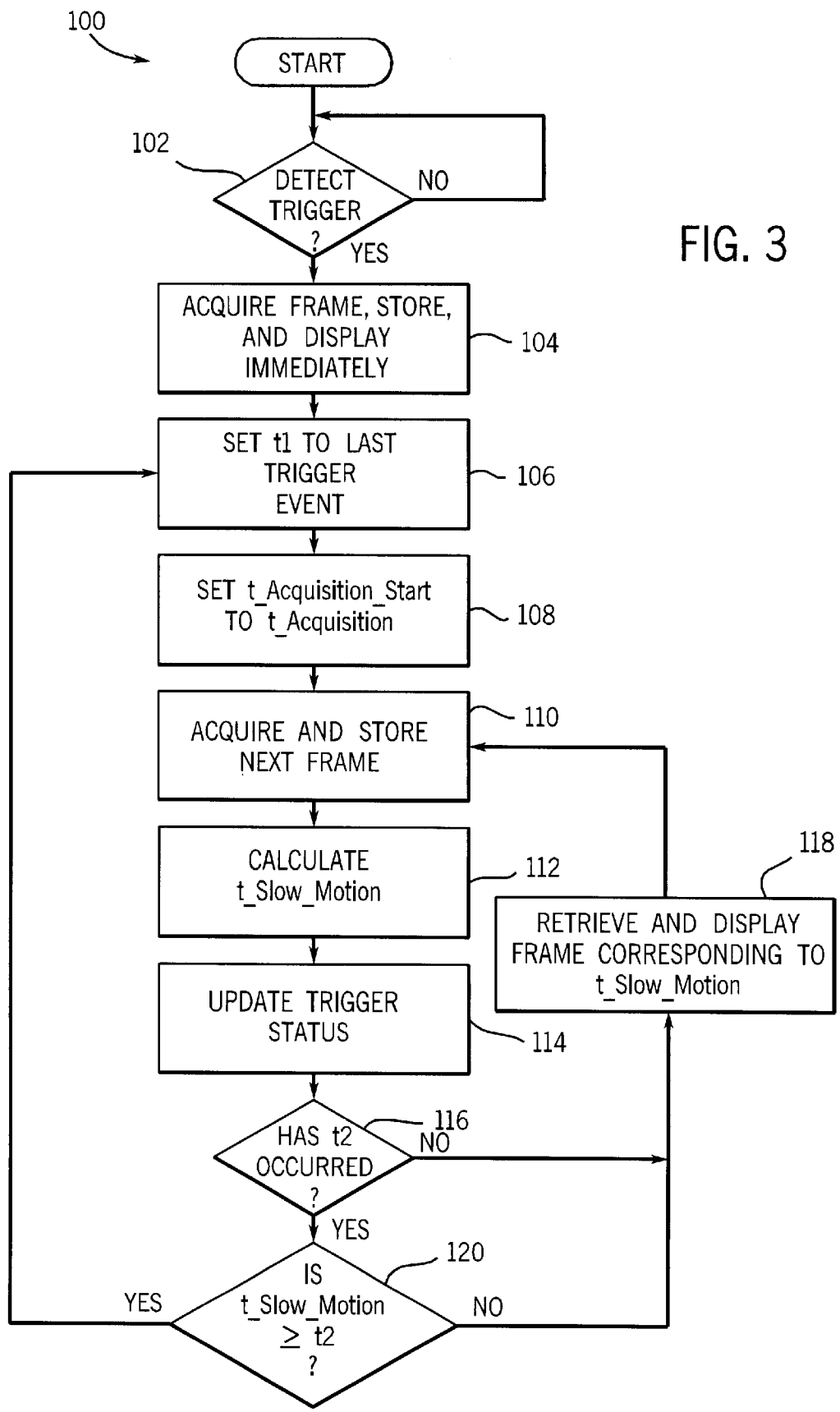
FIG. 3 illustrates a flow chart of a procedure for triggered synchronization of a real-time slow motion display of ultrasound data with ongoing acquisition of ultrasound information according to a preferred embodiment of the present invention.

FIG. 3 illustrates a flow chart of one possible implementation of a triggered synchronization scheme. It should be understood that for each of the synchronization schemes described herein, the acquisition of ultrasound information is preferably ongoing. At 100 the system user activates the real-time slow motion display mode. At 102, the RTSM controller 27 waits for a trigger event generated by the trigger generator 29. At 104, the frame of ultrasound information acquired at that instant is stored in memory 28 and immediately displayed on display 26. At 106, t1 is set to the time of the last trigger event (which will be the trigger event detected at 102 the first time through). At 108, t_Acquisition_Start is set equal to the current acquisition time t_Acquisition. At 110, the next frame of ultrasound information is stored in memory 28. At 112, the RTSM controller 27 determines which stored frame of ultrasound information should be displayed by calculating t_Slow_Motion according to the programmed slow motion factor using the equation described above: t_Slow_Motion=t1+((t_Acquisition-t_Acquisition_Start)/(Slow motion factor)). At 114, the status of the trigger events are updated. At 116, the RTSM controller 27 determines whether trigger event t2 has occurred. If t2 has not yet occurred, then at 118, the frame corresponding to the calculated t_Slow_Motion is retrieved from memory 28 and displayed on display 26 (and the subroutine returns to 110 to acquire and store the next frame.). If t2 has occurred, then at 120, the RTSM controller 27 determines whether the calculated t_Slow_Motion is greater than or equal to t2. If t_Slow_Motion is less than (i.e., prior to) t2, then at 118, the frame corresponding to the calculated t Slow Motion is retrieved from memory 28 and displayed on display 26 (and the subroutine returns to 110 to acquire and store the next frame.). If t_Slow_Motion is greater than or equal to (i.e., falls on or after) t2, then the subroutine returns to 104 where t1 is set to the last detected trigger event and the subroutine continues.

A non-triggered synchronization of the real-time slow motion display may be implemented in a similar manner by simply replacing the triggering events with an automatically generated sequence of events: t1, t2, t3, t4, . . . The automatically generated sequence of events may be pre-selected timing intervals generated by timer 30 (shown in FIG. 1). Selecting an interval between t1, t2, t3, t4, etc. of, for example, 100 ms (t(i)=i*(100 ms)) and a slow motion factor of 10 would provide a slow motion display of a 100 ms period for each full second of acquisition.

Figure 4:
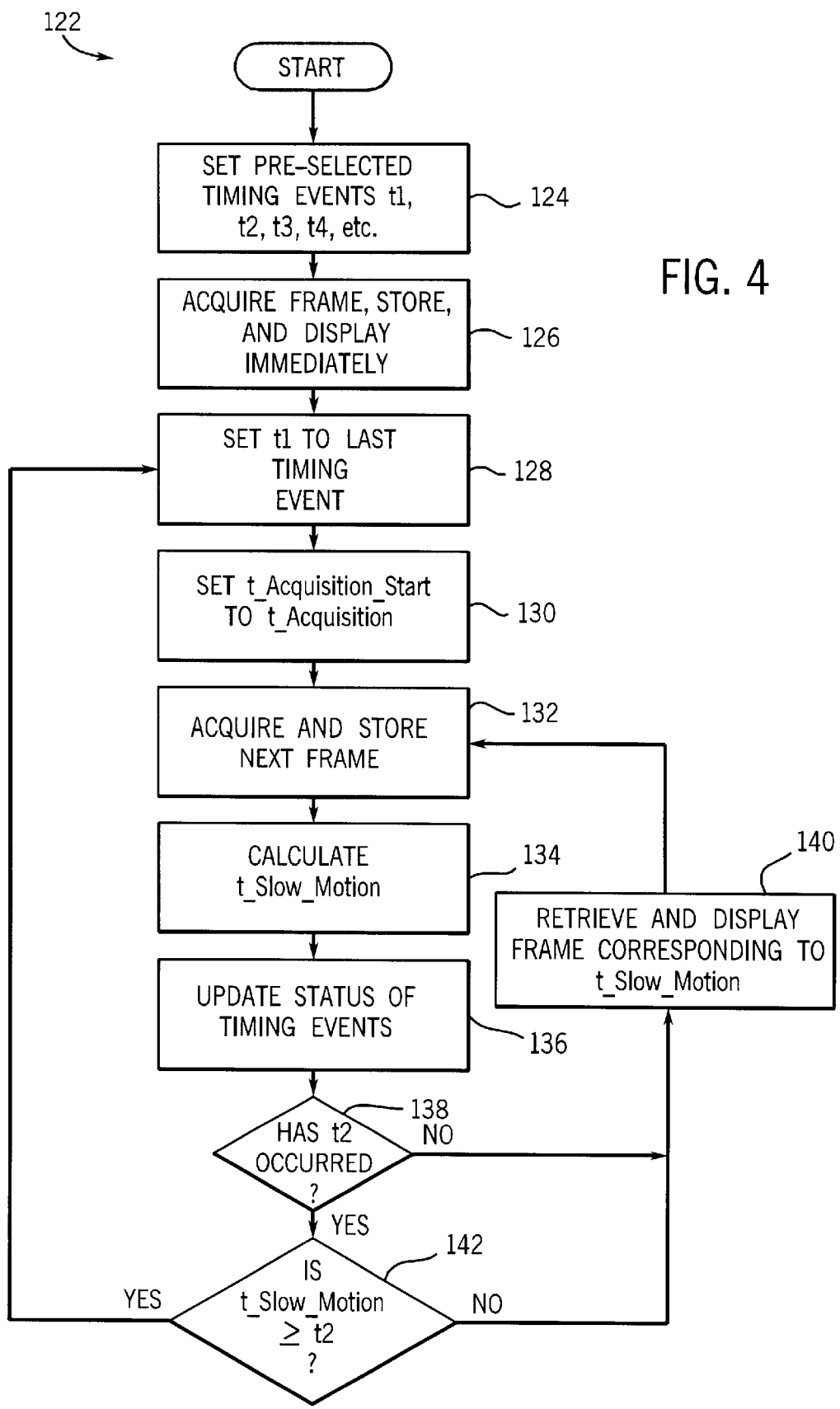
FIG. 4 illustrates a flow chart of a procedure for non-triggered synchronization of a real-time slow motion display of ultrasound data with ongoing acquisition of ultrasound information according to a preferred embodiment of the present invention

FIG. 4 illustrates a flow chart of one possible implementation of a non-triggered synchronization scheme. At 122, the system user activates the real-time slow motion display mode. At 124, a number of pre-selected timing events t1, t2, t3, t4, etc. are set according to intervals programmed by the user. Alternatively, the user could select a single timing interval and the timer 30 would be used to set and update the timing events as the subroutine proceeds. At 126, the frame of ultrasound information acquired at that instant is stored in memory 28 and immediately displayed on display 26. At 128, t1 is set to the time of the last timing event (which will correspond approximately to the start of the subroutine the first time through). At 130, t_Acquisition_Start is set equal to the current acquisition time t_Acquisifion. At 132, the next frame of ultrasound information is stored in memory 28. At 134, the RTSM controller 27 determines which stored frame of ultrasound information should be displayed by calculating t_Slow_Motion according to the programmed slow motion factor using the equation described above: t_Slow_Motion=t1+((t_Acquisition-t_Acquisition_Start)/(Slow motion factor)). At 136, the status of the timing events are updated. At 138, the RTSM controller 27 determines whether timing event t2 has occurred. If t2 has not yet occurred, then at 140, the frame corresponding to the calculated t_Slow_Motion is retrieved from memory 28 and displayed on display 26 (and the subroutine returns to 132 to acquire and store the next frame.). If t2 has occurred, then at 142, the RTSM controller 27 determines whether the calculated t_Slow_Motion is greater than or equal to t2. If t_Slow_Motion is less than (i.e., prior to) t2, then at 140, the frame corresponding to the calculated t_Slow_Motion is retrieved from memory 28 and displayed on display 26 (and the subroutine returns to 132 to acquire and store the next frame.). If t_Slow_Motion is greater than or equal to (i.e., falls on or after) t2, then the subroutine returns to 128 where t1 is set to the last timing event and the subroutine continues.

Figure 5:
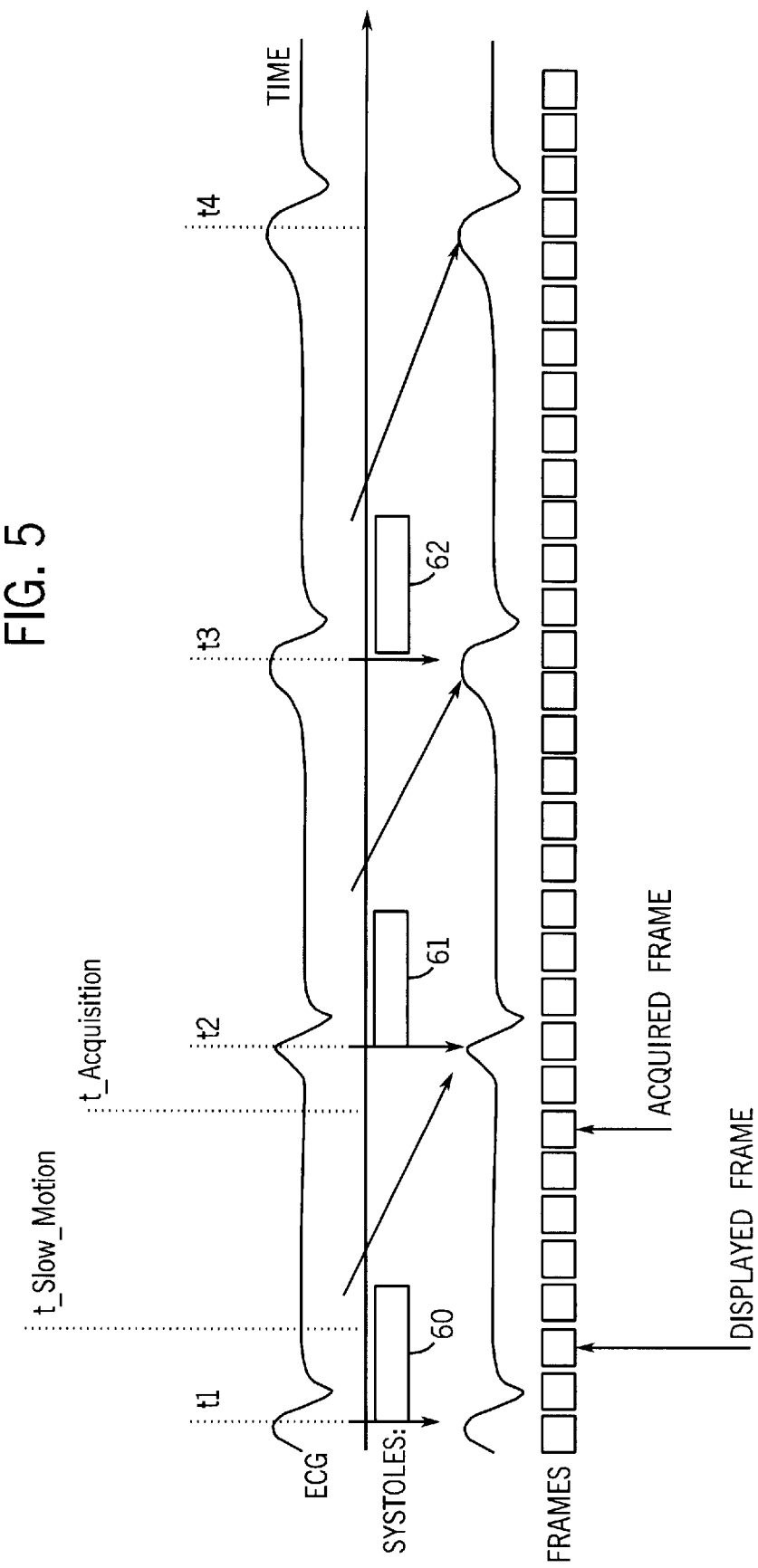
FIG. 5 illustrates a timing diagram of a procedure for synchronizing a real-time slow motion display of ultrasound data with ongoing acquisition of ultrasound information according to a preferred embodiment of the present invention.
Figure 6:
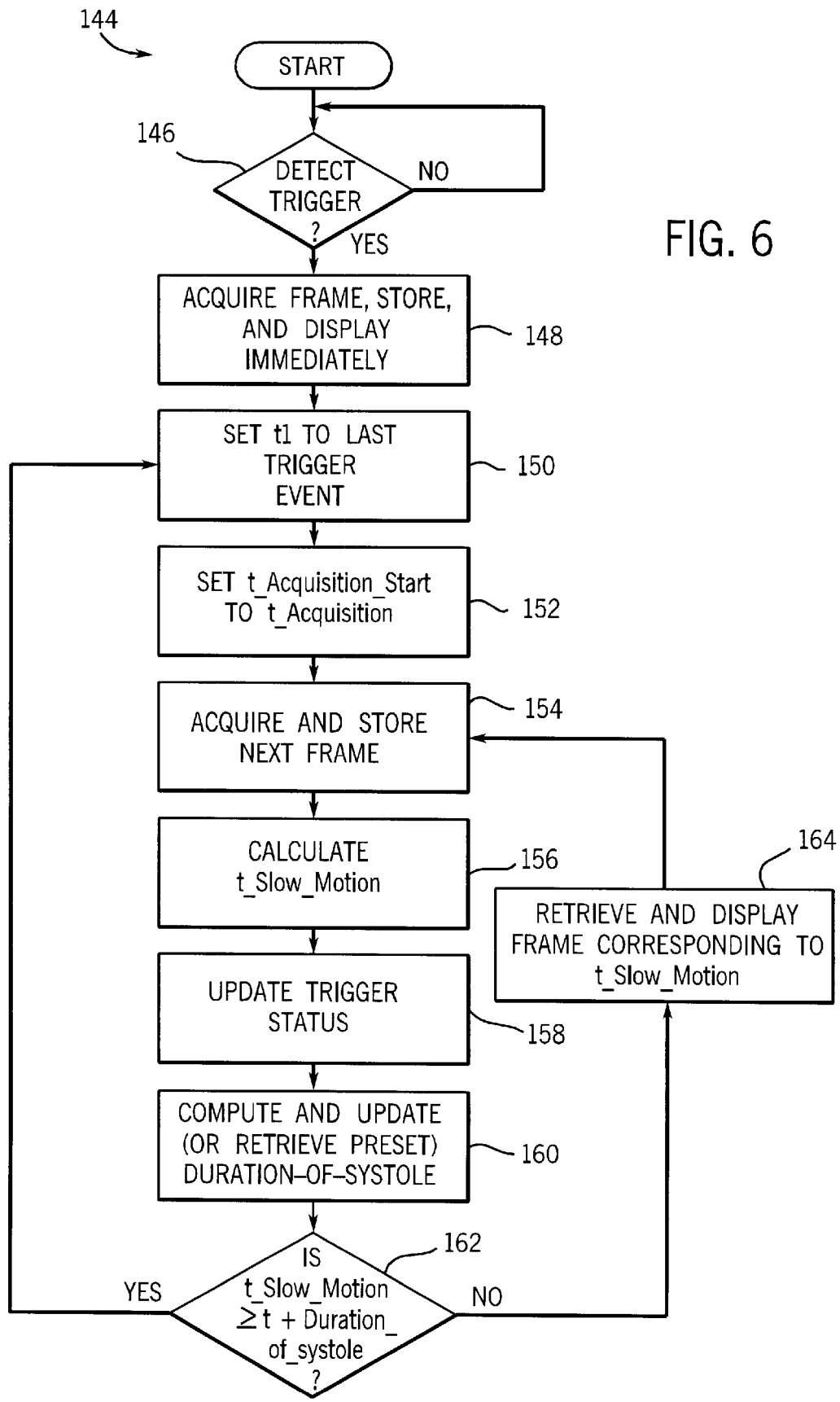
FIG. 6 illustrates a flow chart of a procedure for triggered synchronization of a real-time slow motion display of ultrasound data with ongoing acquisition of ultrasound information according to a preferred embodiment of the present invention.

FIG. 5 illustrates a different synchronization mechanism for real-time slow motion. In general, one or more time intervals can be specified relative to the triggering points and used to define the duration of each segment of real-time slow motion display instead of the complete time intervals defined by the intervals between triggering events t1 and t2, t2 and t3, etc. FIG. 5 provides an example of an interval selection that would be useful in, for example, cardiac imaging where it is often desirable to focus on the systolic part of the heartbeat. Intervals 60, 61, and 62 of FIG. 5 correspond to the systolic part of the heartbeat. Systole is approximately 300 ms in duration and represents about one-third of the total heartbeat cycle. The systolic fraction of the heartbeat depends on heart rate, but the duration is relatively independent of heart rate. Similarly, vascular imaging applications can use the systole to focus on the pulsatile flow and skip the diastolic periods with reduced flow. The triggered slow motion display algorithm described with respect to FIGS. 2 and 3 may be adapted as shown in FIG. 5 and 6 to display systolic slow motion by replacing the test:

$$t\_Slow\_Motion \geq t2$$

with:

$$t\_Slow\_Motion \geq (t1+Duration\_of\_systole).$$

The Duration_of_Systole is illustrated in FIG. 5 as the intervals 60, 61 and 62. Any slow motion factor may be used, but it can be of particular interest to compute and continuously update according to:

Slow motion factor=(t2−t1)/(Duration of systole)

This specific slow motion factor will make it possible to display systole continuously during the complete heart cycle.

FIG. 6 illustrates a flow chart of one possible implementation of a triggered synchronization scheme adapted to display the systolic portion of a heartbeat. It should be understood that this scheme may be modified to display other intervals corresponding to other physiological events. At 144, the system user activates the real-time slow motion display mode. At 146, the RTSM controller 27 waits for a trigger event generated by the trigger generator 29. At 148, the frame of ultrasound information acquired at that instant is stored in memory 28 and immediately displayed on display 26. At 150, t1 is set to the time of the last trigger event (which will be the trigger event detected at 146 the first time through). At 152, t_Acquisition_Start is set equal to the current acquisition time t_Acquisition. At 154, the next frame of ultrasound information is stored in memory 28. At 156, the RTSM controller 27 determines which stored frame of ultrasound information should be displayed by calculating t_Slow_Motion using the equation described above: t_Slow_Motion=t1+((t_Acquisition-t_Acquisition_Start)/(Slow motion factor)). The slow motion factor may be preset or, alternatively, the slow motion factor could be computed and updated continuously as described above according a dynamic duration of systole as detected by, for example, and ECG or phono trace. At 158, the status of the trigger events are updated. At 160, the duration of systole is computed and updated or, if preset, is retrieved. At 162, the RTSM controller 27 determines whether the calculated t_Slow_Motion is greater than or equal to t1 plus the duration of systole determined at 160. If t_Slow_Motion is less than (i.e., prior to) t1 plus the duration of systole, then at 164, the frame corresponding to the calculated t_Slow_Motion is retrieved from memory 28 and displayed on display 26 (and the subroutine returns to 154 to acquire and store the next frame.). If t_Slow_Motion is greater than or equal to (i.e., falls on or after) t1 plus the duration of systole, then the subroutine returns to 150 where t1 is set to the last detected trigger event and the subroutine continues.

It may also be advantageous to specify a synchronization scheme that guarantees that at least some portion of all heartbeats will be displayed. One way to accomplish this is to use t_Acquisition≧t2 as the criterion for restarting the synchronization procedure. When t_Acquisition is greater than or equal to t2, t1 is reset to the last detected trigger event, t_Acquisition_Start is set to the current acquisition time (t_Acquisition) and t_Slow_Motion is recomputed using the updated values. These steps are then repeated each time t_Acquisition is greater than or equal to t2.

Figure 7:
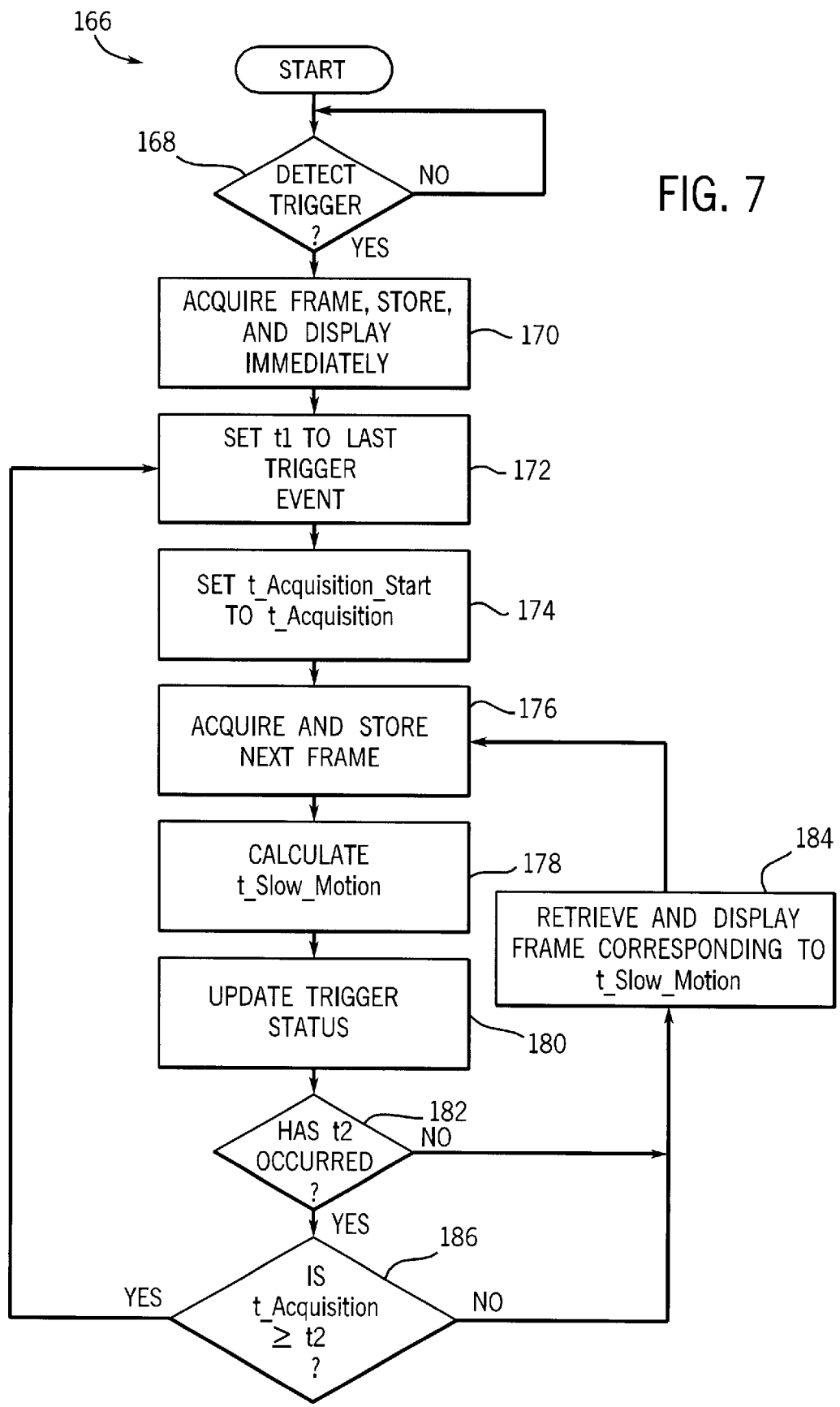
FIG. 7 illustrates a flow chart of a procedure for triggered synchronization of a real-time slow motion display of ultrasound data with ongoing acquisition of ultrasound information according to a preferred embodiment of the present invention.

FIG. 7 illustrates a flow chart of one possible implementation of a triggered synchronization scheme that guarantees that at least some portion of all heartbeats will be displayed. At 166 the system user activates the real-time slow motion display mode. At 168, the RTSM controller 27 waits for a trigger event generated by the trigger generator 29. At 170, the frame of ultrasound information acquired at that instant is stored in memory 28 and immediately displayed on display 26. At 172, t1 is set to the time of the last trigger event (which will be the trigger event detected at 168 the first time through). At 174, t_Acquisition_Start is set equal to the current acquisition time t_Acquisition. At 176 the next frame of ultrasound information is stored in memory 28. At 178, the RTSM controller 27 determines which stored frame of ultrasound information should be displayed by calculating t_Slow_Motion according to the programmed slow motion factor using the equation described above: t_Slow_Motion=t1+((t_Acquisition-t_Acquisition_Start)/(Slow motion factor)). The slow motion factor may be preset or, alternatively, the slow motion factor could be computed and updated continuously as described above according a dynamic duration of systole as detected by, for example, and ECG or phono trace. At 180, the status of the trigger events are updated. At 182, the RTSM controller 27 determines whether trigger event t2 has occurred. If t2 has not yet occurred, then at 184, the frame corresponding to the calculated t_Slow_Motion is retrieved from memory 28 and displayed on display 26 (and the subroutine returns to 176 to acquire and store the next frame.). If t2 has occurred, then at 186, the RTSM controller 27 determines whether the t_Acquisition is greater than or equal to t2. If t_Acquisition is less than (i.e., prior to) t2, then at 184, the frame corresponding to the calculated t_Slow_Motion is retrieved from memory 28 and displayed on display 26 (and the subroutine returns to 176 to acquire and store the next frame.). If t_Acquisition is greater than or equal to (i.e., falls on or after) t2, then the subroutine returns to 172 where t1 is set to the last detected trigger event and the subroutine continues.

It may also be useful to have real-time slow motion display of time intervals that extend across a triggering event. Typically, one would be interested in the 50–100 ms prior to the R-event in ECG triggering in addition to a time interval like systole that starts at the R-event. Slow motion display of an interval that extends across a triggering event may be accomplished with the following adjusted formula for conversion from acquisition time to the corresponding slow motion time (t_Slow_Motion):

$$t\_Slow\_Motion = t1 + t\_delta + ((t\_Acquisition - t\_Acquisition\_Start)/(Slow\ motion\ factor))$$

By specifying a t_delta equal to −100 ms, for example, the atrial contraction could be included in a real-time slow motion display of systole. The parameter t_delta might also be computed adaptively in order to make "t1+t_delta" correspond to the P-event in the P-Q-R-S-T ECG complex. This possibility is particularly advantageous in order to obtain "flicker free" real-time slow motion display of complete heart cycles. The p-event occurs in the quietest diastolic period and, therefore, the switch to a future heart cycle during resynchronization will most likely avoid annoying synchronization flicker.

Figure 8:
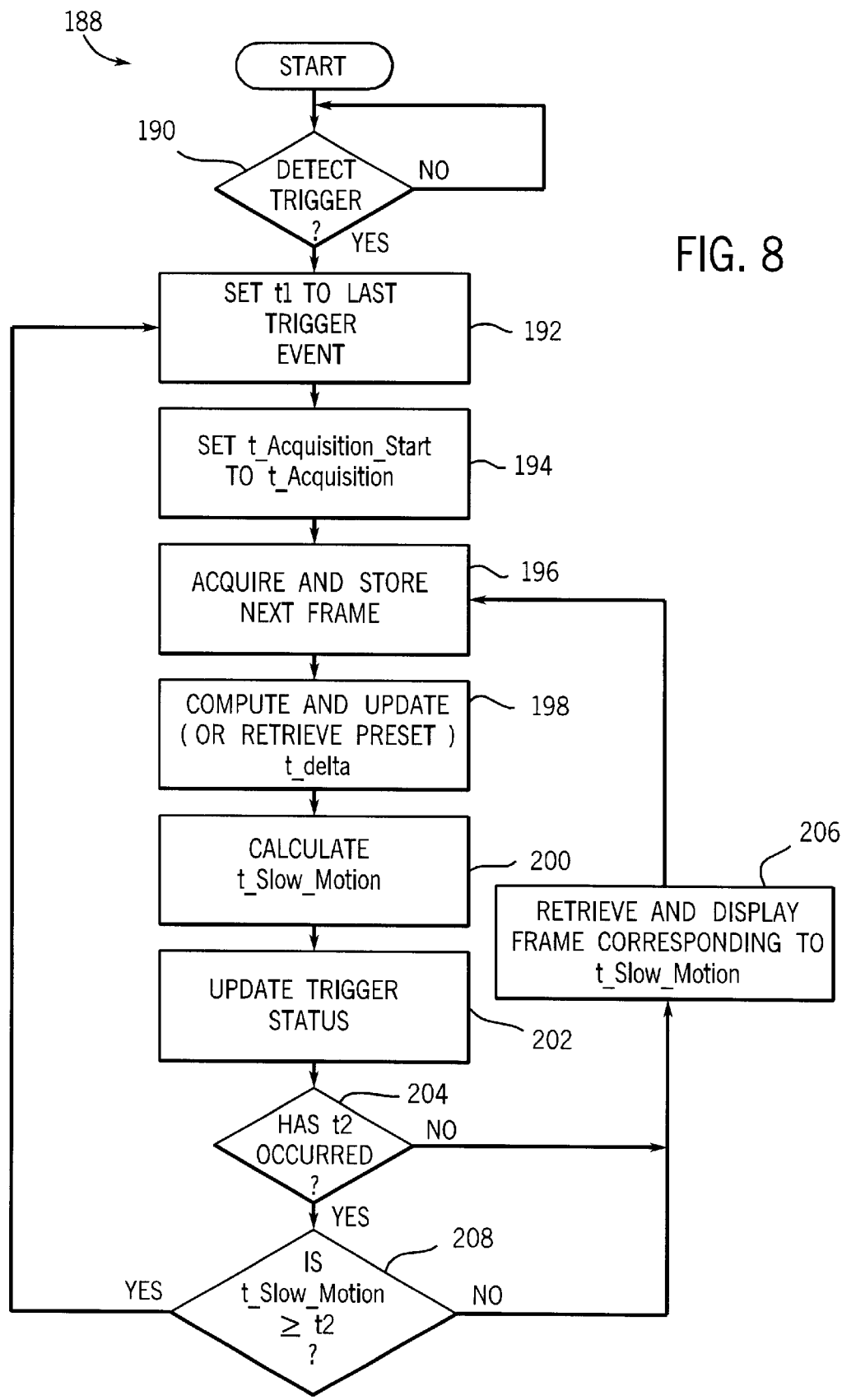
FIG. 8 illustrates a flow chart of a procedure for triggered synchronization of a real-time slow motion display of ultrasound data with ongoing acquisition of ultrasound information according to a preferred embodiment of the present invention.

FIG. 8 illustrates a flow chart of one possible implementation of a triggered synchronization scheme that will allow a display of time intervals that extend across a trigger event. At 188, the system user activates the real-time slow motion display mode. At 190, the RTSM controller 27 waits for a trigger event generated by the trigger generator 29. For this example, it is preferable although not necessary that the acquisition and storage of ultrasound information has been ongoing for a short period of time (at least one heart cycle) immediately prior to activation of the real-time slow motion mode to allow the display of frames which have occurred prior to the trigger event detected at 190. At 192, t1 is set to the time of the last trigger event (which will be the trigger event detected at 190 the first time through). At 194, t_Acquisition_Start is set equal to the current acquisition time t_Acquisition. At 196 the next frame of ultrasound information is stored in memory 28. At 198, t_delta is computed and updated or, if preset, retrieved. At 200, the RTSM controller 27 determines which stored frame of ultrasound information should be displayed by calculating t_Slow_Motion according to the programmed slow motion factor using the equation described above: t_Slow_Motion=t1+t_delta+((t_Acquisition−t_Acquisition_Start)/(Slow motion factor)). At 202 the status of the trigger events are updated. At 204, the RTSM controller 27 determines whether trigger event t2 has occurred. If t2 has not yet occurred, then at 206, the frame corresponding to the calculated t_Slow_Motion is retrieved from memory 28 and displayed on display 26 (and the subroutine returns to 196 to acquire and store the next frame.). If t2 has occurred, then at 208, the RTSM controller 27 determines whether the calculated t_Slow_Motion is greater than or equal to t2. If t_Slow_Motion is less than (i.e., prior to) t2, then at 206, the frame corresponding to the calculated t_Slow_Motion is retrieved from memory 28 and displayed on display 26 (and the subroutine returns to 196 to acquire and store the next frame.). If t_Slow_Motion is greater than or equal to (i.e., falls on or after) t2, then the subroutine returns to 192 where t1 is set to the last detected trigger event and the subroutine continues. Alternatively, for an application where it is desirable to view only the P-Q-R-S-T complex, step 204 could be substituted by a step which computes and updates the interval between R and T in the ECG complex or retrieves a preset R-T interval and synchronization condition, t_Slow_Motion≧t2, at step 208 could be modified to t_Slow_Motion≧t1+R-T interval. Other similar modification to the implementations described with respect to FIGS. 2–8 should be apparent to one of skill in the art.

Figure 9:
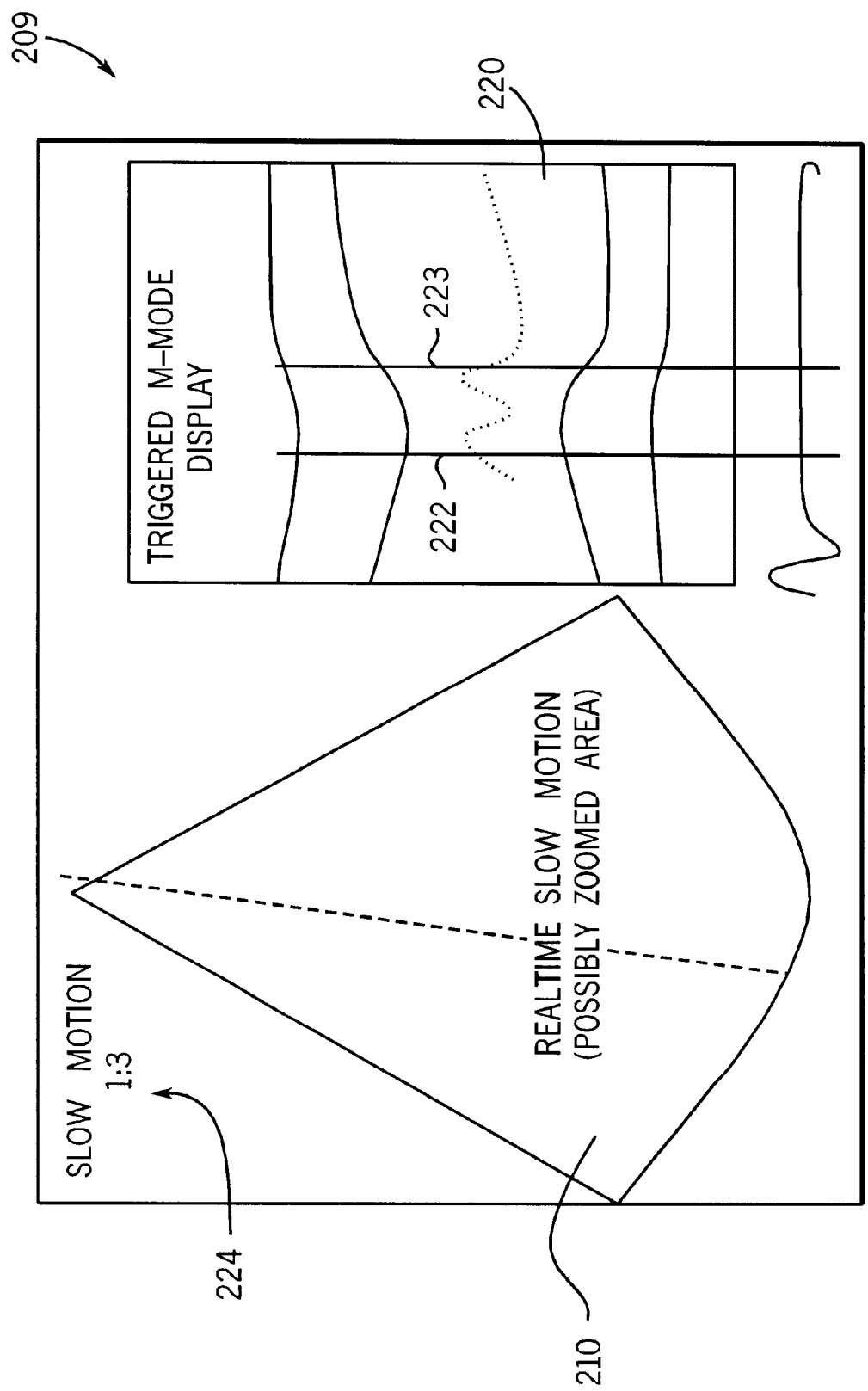
FIG. 9 illustrates a display having a real-time slow motion display region and a triggered M-mode region according to a preferred embodiment of the present invention.

In addition to the display of the real-time slow images, a triggered MMode image may be used to give visual feedback of the selected time intervals and triggering events and as a user interface for specifying the time interval. FIG. 9 illustrates one possible graphical implementation of a triggered M-Mode display. As shown in FIG. 9 an ultrasound display 209 includes a real time slow motion display region 210 and a triggered M-Mode display region 220. Vertical lines 222 and 223 in the triggered M-Mode display region 220 indicate visual feedback of the selected time intervals and provide a possibility for manual user adjustments. The selected slow motion factor is displayed in the upper left hand corner at 224.

Real-time display of ultrasound in slow motion may also be used in combination with computationally intensive image processing. The processing associated with the acquired ultrasound information (Doppler processing, envelope detection, spatial filtering, temporal filtering, scan conversion, computing derived information like an image with blood/tissue segmentation etc.) can, depending on the modality and hardware, be too demanding compared with the frame-rate that can be achieved by the acquisition unit. The present invention may provide full real-time viewing in these computationally intensive situations. In order to implement full realtime viewing of ultrasound information processed in a computationally intensive manner, the synchronization procedures described above may be used, except that the equation for t_Slow_Motion must be modified such that it equals the time associated with the last image frame that has completed the processing pipeline and is ready for display.

Figure 10:
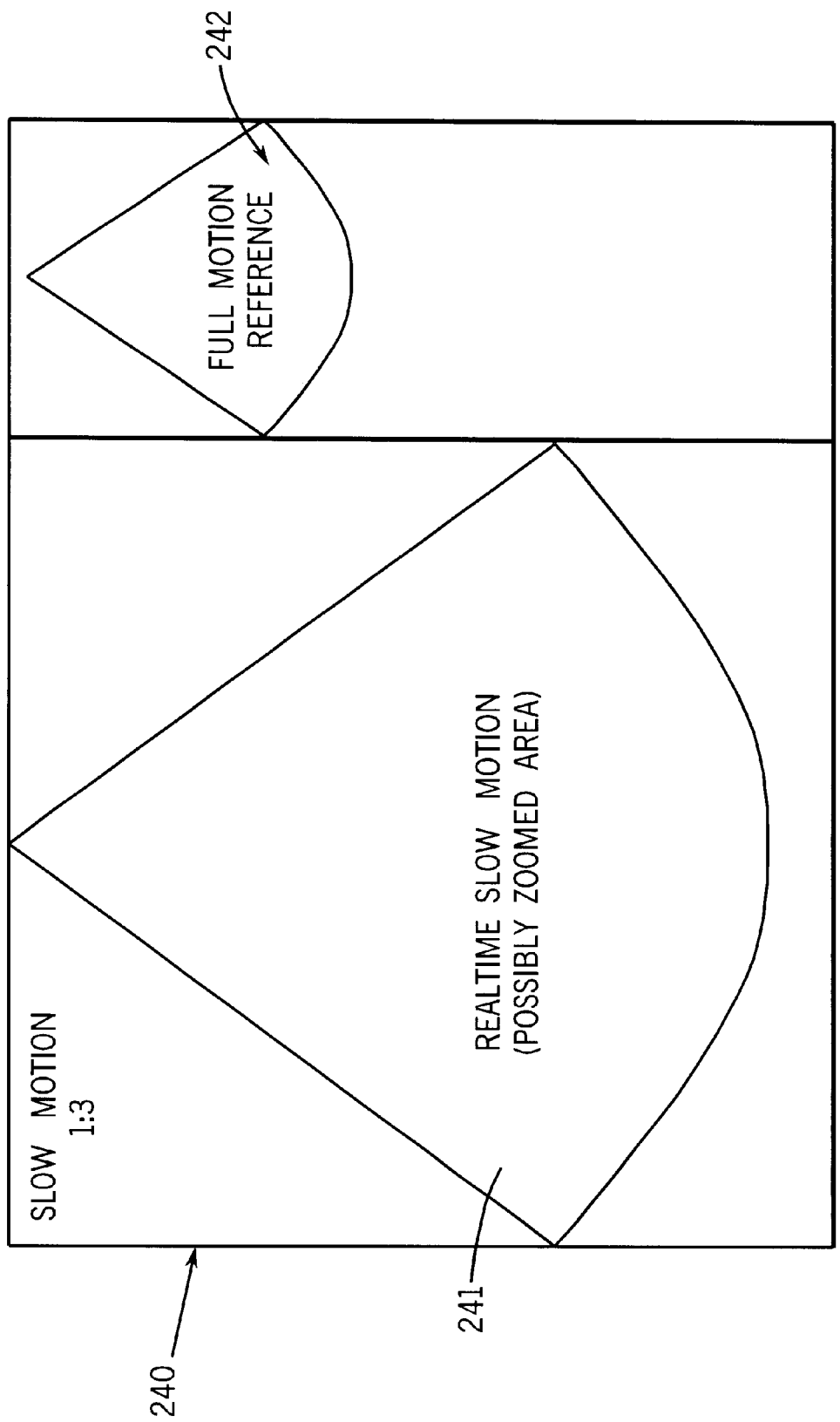
FIG. 10 illustrates a display having a real-time slow motion display region and a live display region according to a preferred embodiment of the present invention.

The real-time slow motion display usually makes it necessary to skip some heart cycles that are acquired during the slow motion display of a previous cycle. FIG. 10 illustrates how a real-time slow motion image 241 and a true live image 242 could be combined on a single display 240. The slow motion image 241 could be selected by the user as a zoomed region in the live image. A zoomed slow motion display can, for example, be useful for generation of an optimal display of heart valves inside the image.

Figure 11:
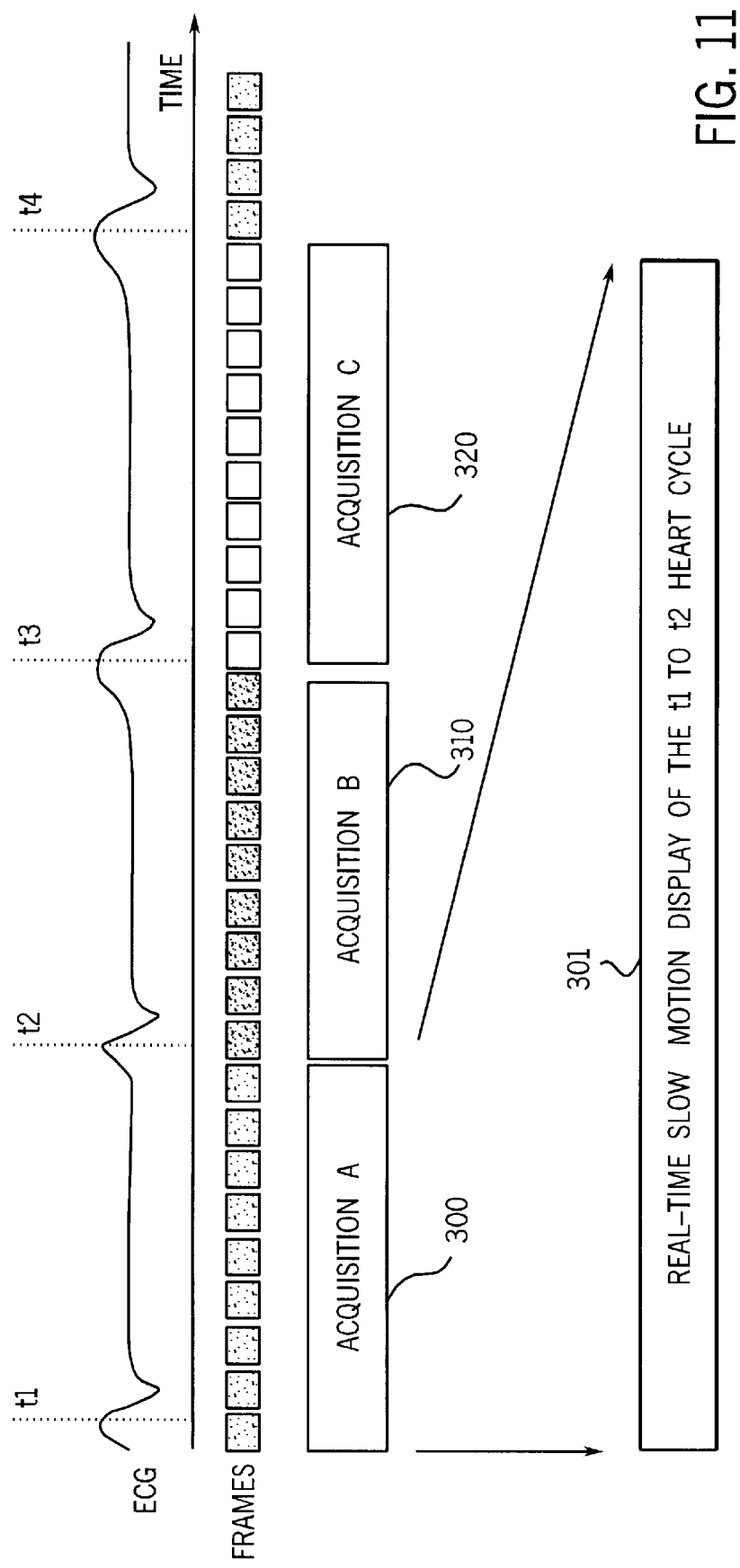
FIG. 11 illustrates a timing diagram of a procedure for synchronizing a real-time slow motion display of ultrasound data with ongoing acquisition of ultrasound information in one or more different acquisition modes according to a preferred embodiment of the present invention.

FIG. 11 illustrates how the real-time slow motion display technique can be utilized to simultaneously acquire multiple modalities. FIG. 11 provides an example of real-time slow motion display of complete heart cycles. A slow motion factor of 3 is selected. This means that every third heart beat will be displayed in slow motion. Thus, as shown in FIG. 11, the frames of a first heart beat, which are acquired during the period Acquisition A (300) between trigger events t1 and t2, are displayed in slow motion over the period 301 between trigger events t1 and t4. The image frames acquired during periods Acquisition B (310) and Acquisition C (320) are not displayed in slow motion (although they may be displayed in a separate live display as in FIG. 10). However, acquisition continues during the two non-displayed heart beats corresponding to periods Acquisition B (310) and Acquisition C (320). The acquired non-displayed frames may be stored in memory and made available for subsequent replay viewing.

The acquisition mode and the type of information acquired during periods Acquisition B (310) and Acquisition C (320) may be the same as for the period Acquisition A (300). Alternatively, the acquisition mode and the type of information acquired during periods Acquisition B (310) and Acquisition C (320) may be altered. Since it can be determined at the time t_Acquisition passes a trigger event whether the next heart cycle will be included in the slow motion display, it is therefore possible for the scanner to change acquisition mode for heart cycles that are excluded from the slow motion display. For example, in FIG. 11, the acquisition mode during period Acquisition A (300) may be changed to a different modality during period Acquisition B (310) and possibly to a third modality during period Acquisition C (320). The following are some examples of useful modality combinations: high frame-rate 2D for real-time slow motion combined with maximum 2D image quality; 2D tissue combined with color flow modalities (blood flow, B-flow, tissue velocity, strain, blood motion imaging, etc.); any 2D modality and spectral Doppler; or any 2D modality and M-Mode. Information acquired according to the different modalities could be combined in a single display during live scanning and presented to the user in, for example, the manner illustrated in FIGS. 9 or 10. Alternatively, the information acquired during acquisition periods that are not included in the real-time slow motion display could be stored and made available for viewing and analysis during replay.

Stress echo is an example of a situation where it is of particular interest to combine acquisition modalities. The user will typically prefer high quality tissue 2D as the viewing modality both during the actual acquisition and replay viewing. Nevertheless, it will be advantageous if modalities such as tissue velocity imaging and strain imaging still can be acquired and made available for viewing and quantification of wall motion and wall thickening. The multi-modality acquisition technique described above can be used to accomplish this goal. An example of one possible acquisition and display technique that could be used for stress echo is given with respect to FIG. 11. Still, the user might be interested in viewing high quality 2D at the original frame-rate while additional information sources like tissue velocity imaging and strain imaging are acquired in the background. This goal can be implemented by making the display frame-rate equal to the acquisition frame-rate (i.e., slow motion factor is equal to 1) and then, at each synchronization step, repeating playback of the high quality tissue 2D tissue as long as the acquisition of the other modalities have not completed. The synchronization step is performed as specified for real-time slow motion at the first trigger event after completion of all the specified acquisition setups. As a result, the user will experience continuous flicker-free tissue 2D imaging. The display will alternate between live display and live playback while other modalities are acquired.

In the foregoing specification the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarding in an illustrative rather than restrictive sense.

What is claimed is:

1. A method of displaying ultrasound information comprising:
    acquiring ultrasound information at an acquisition rate;
    displaying at least a portion of said ultrasound information at a display rate less than said acquisition rate while continuously acquiring said ultrasound information; and
    synchronizing the display of ultrasound information with the acquisition of ultrasound information.

2. The method according to claim 1 wherein the display of ultrasound information is synchronized with the acquisition of ultrasound information upon satisfaction of a synchronization condition.

3. The method according to claim 2, wherein the synchronization condition relates to a physiological event.

4. The method according to claim 3 further comprising:
    providing a simultaneous display of a triggered M-mode; and
    selecting a physiological event from a plurality of physiological events displayed on the triggered M-mode display.

5. The method according to claim 2, wherein the synchronization condition relates to a timed event.

6. The method according to claim 1, further comprising:
    detecting a physiological event; and
    generating a trigger event upon each detection of a physiological event
    wherein the display of ultrasound information is synchronized with the acquisition of ultrasound information upon satisfaction of a synchronization condition associated with a trigger event.

7. The method according to claim 6 wherein the synchronization condition is satisfied when the ultrasound information currently being displayed was acquired on or after a trigger event.

8. The method according to claim 6 wherein the synchronization condition is satisfied when the ultrasound information currently being displayed was acquired on or after a trigger event plus an interval of interest.

9. The method according to claim 1, further comprising:
    detecting a physiological event; and
    generating a trigger event upon each detection of a physiological event;
    wherein the display of ultrasound information is synchronized with the acquisition of ultrasound information upon the occurrence of each trigger event.

10. The method according to claim 7, wherein the physiological event is a predefined portion of a heart cycle.

11. The method according to claim 1, wherein said acquisition rate is higher than the maximum perception rate of the human eye and said display rate is lower than or equal to said maximum perception rate.

12. The method according to claim 1, wherein said acquisition rate is higher than a standard video frame rate and said display rate is lower than or equal to said standard video frame rate.

13. The method according to claim 1, wherein said display rate is determined by a programmable slow motion factor defined as a ratio of the acquisition rate to the display rate.

14. The method according to claim 1, wherein said display rate is adaptively determined by a slow motion factor defined as a ratio of the acquisition rate to the display rate farther comprising:
   determining a duration of physiological interval;
   determining a duration of an interval of interest within said physiological interval; and
   calculating the slow motion factor by dividing the duration of said physiological interval by the duration of the interval of interest.

15. The method according to claim 14, wherein said physiological interval is an R to R interval of a heart cycle and the interval of interest is a systolic portion of a heart cycle.

16. The method according to claim 1 further comprising:
   simultaneously displaying said acquired ultrasound information at a display rate equal to said acquisition rate.

17. A method of presenting ultrasound information comprising:
   detecting a trigger event and defining a corresponding first trigger time;
   acquiring and immediately displaying a first frame of ultrasound information upon said trigger event;
   acquiring a second frame of ultrasound information at a consecutive acquisition time;
   storing said second frame according to its acquisition time; and
   displaying said second frame when the first trigger time added to a quotient of an elapsed time from said trigger event divided by a slow motion factor is equal to the acquisition time of the second frame.

18. The method according to claim 17 further comprising:
   (a) acquiring subsequent frames of ultrasound information;
   (b) displaying a subsequent frame when the first trigger time added to a quotient of an elapsed time from said trigger event divided by a slow motion factor is equal to the respective acquisition time of the subsequent frame;
   (d) repeating steps (a) and (b) while waiting for the detection of a second trigger event;
   (e) upon detection of said second trigger event, redefining the first trigger time as the time of the second trigger event;
   (f) acquiring and immediately displaying a frame of ultrasound information; and
   (g) repeating steps (a) through (f).

19. The method according to claim 17 further comprising:
   (a) detecting subsequent trigger events;
   (b) acquiring subsequent frames of ultrasound information;
   (c) displaying a subsequent frame when the first trigger time added to a quotient of an elapsed time from said trigger event divided by a slow motion factor is equal to the respective acquisition time of the subsequent frame;
   (d) defining a second trigger time based upon the detection of a second trigger event;
   (e) comparing the second trigger time to the respective acquisition time of the subsequent frame currently being displayed;
   (f) repeating steps (a) through (e) until satisfaction of a synchronization condition that is satisfied when the respective acquisition time of the subsequent frame currently being displayed is greater than or equal to the second trigger time;
   (g) upon satisfaction of the synchronization condition, redefining the first trigger time as the time of a most recently detected trigger event;
   (h) acquiring and immediately displaying a frame of ultrasound information; and
   (i) repeating steps (a) through (h).

20. The method according to claim 17 further comprising:
   (a) detecting subsequent trigger events;
   (b) acquiring subsequent frames of ultrasound information;
   (c) displaying a subsequent frame when the first trigger time added to a quotient of an elapsed time from said trigger event divided by a slow motion factor is equal to the respective acquisition time of the subsequent frame;
   (d) defining an interval of interest;
   (e) comparing the sum of the first trigger time and the interval of interest to the respective acquisition time of the subsequent frame currently being displayed;
   (f) repeating steps (a) through (e) until satisfaction of a synchronization condition that is satisfied when the respective acquisition time of the subsequent frame currently being displayed is greater than or equal to the sum of the first trigger time and the interval of interest;
   (g) upon satisfaction of the synchronization condition, redefining the first trigger time as the time of a most recently detected trigger event;
   (h) acquiring and immediately displaying a frame of ultrasound information; and
   (i) repeating steps (a) through (h).

21. The method according to claim 20, wherein the interval of interest is related to a duration of a systolic event in a heart cycle.

22. The method of presenting ultrasound information comprising:
   (a) waiting for the detection of trigger events;
   (b) acquiring frames of ultrasound information;
   (c) storing said frames together with their respective acquisition times;
   (d) upon detection of a first trigger event defining a first trigger time,
   (e) displaying frames corresponding to an acquisition time equal to the first trigger time added to a quotient of an elapsed time from said trigger event divided by a slow motion factor minus a predetermined delta interval;
   (f) defining a second trigger time based upon the detection of a second trigger event;
   (g) comparing the second trigger time to the respective acquisition time of the frame currently being displayed;
   (h) repeating steps (a) through (g) until satisfaction of a synchronization condition;
   (i) upon satisfaction of the synchronization condition, redefining the first trigger time as the time of a most recently detected trigger event; and
   (j) repeating steps (a) through (i).

23. The method according to claim 22, wherein the synchronization condition is satisfied when the respective acquisition time of the frame currently being displayed is greater than or equal to the second trigger time.

24. The method according to claim 22, wherein the synchronization condition is satisfied when the respective acquisition time of the frame currently being displayed is greater than or equal to the first trigger time plus an interval of interest.

25. The method according to claim 24, wherein the interval of interest is adaptively determined.

26. The method according to claim 22, wherein the trigger event corresponds to an R-wave and the delta interval corresponds to the P to R interval of a cardiac cycle.

27. A method of acquiring and displaying ultrasound information:

acquiring ultrasound information at an acquisition rate according to a first mode during a first acquisition period;

acquiring ultrasound information according to a second mode, which is different from said first mode, during a second acquisition period; and displaying the ultrasound information acquired during said first acquisition period at a display rate that is lower than said acquisition rate such that at least a portion of the ultrasound information acquired during said first acquisition period is displayed during said first acquisition period and at least a portion of the ultrasound information acquired during said first acquisition period is displayed during said second acquisition period.

28. The method according to claim 27 further comprising: storing the ultrasound information acquired during said second acquisition period.

29. The method according to claim 27 wherein the first and second acquisition periods correspond to an interval between physiological events.

30. The method according to claim 27 wherein the first and second acquisition periods correspond to a predetermined time interval.

31. The method according to claim 27 wherein at least one frame of ultrasound information acquired during said first acquisition period is displayed immediately after its acquisition.

32. A method of acquiring, processing and displaying ultrasound information comprising:

acquiring ultrasound information at an acquisition rate;

processing said ultrasound information at a processing rate that is lower than said acquisition rate;

displaying said ultrasound information at a display rate that is the same as or lower than said processing rate while continuously acquiring said ultrasound information; and synchronizing the processing of ultrasound information with the acquisition of ultrasound information.

33. The method according to claim 32 wherein the processing of ultrasound information is synchronized with the acquisition of ultrasound information upon satisfaction of a synchronization condition.

34. The method according to claim 33, wherein the synchronization condition relates to a physiological event.

35. The method according to claim 33, wherein the synchronization condition relates to a timed event.

36. The method according to claim 32, further comprising:

detecting a physiological event; and generating a trigger event upon each detection of a physiological event;

wherein the processing of ultrasound information is synchronized with the acquisition of ultrasound information upon satisfaction of a synchronization condition associated with a trigger event.

37. The method according to claim 36 wherein the synchronization condition is satisfied when the ultrasound information currently being processed was acquired on or after a trigger event.

38. The method according to claim 36 wherein the synchronization condition is satisfied when the ultrasound information currently being processed was acquired on or after a trigger event plus an interval of interest.

* * * * *